United States Patent
Liu et al.

(10) Patent No.: US 9,393,312 B2
(45) Date of Patent: Jul. 19, 2016

(54) AMPHIPHILIC BLOCK COPOLYMER AND PREPARATION METHOD THEREOF AND MICELLAR DRUG-LOADING SYSTEM FORMED BY SAME WITH ANTITUMOR DRUG

(71) Applicant: Suzhou Nanomedicine R&D Co., Ltd., Suzhou (CN)

(72) Inventors: Ke Liu, Suzhou (CN); Feirong Gong, Suzhou (CN); Hui Xu, Suzhou (CN); Yuewu Lang, Suzhou (CN); Huaying Fan, Suzhou (CN); Fei Han, Suzhou (CN); Xin Che, Suzhou (CN)

(73) Assignees: SUZHOU NANOMEDICINE R&D CO., LTD., Suzhou, Jiangsu (CN); CHANGZHOU TARGET MEDICINE TECHNOLOGY CO., LIMITED, Changzhou, Jiangsu Province (CN)

( * ) Notice: Subject to any disclaimer, the term of this patent is extended or adjusted under 35 U.S.C. 154(b) by 0 days.

(21) Appl. No.: 14/438,409

(22) PCT Filed: Sep. 22, 2013

(86) PCT No.: PCT/CN2013/083958
§ 371 (c)(1),
(2) Date: Apr. 24, 2015

(87) PCT Pub. No.: WO2014/063549
PCT Pub. Date: May 1, 2014

(65) Prior Publication Data
US 2015/0283246 A1    Oct. 8, 2015

(30) Foreign Application Priority Data
Oct. 26, 2012 (CN) .......................... 2012 1 0414318

(51) Int. Cl.
| | |
|---|---|
| A61K 47/30 | (2006.01) |
| A61K 47/34 | (2006.01) |
| A61K 47/42 | (2006.01) |
| C08G 63/664 | (2006.01) |
| C08G 64/18 | (2006.01) |
| A61K 9/107 | (2006.01) |
| A61K 9/19 | (2006.01) |
| A61K 31/09 | (2006.01) |
| A61K 31/337 | (2006.01) |
| A61K 31/704 | (2006.01) |
| C08G 63/82 | (2006.01) |
| C08G 63/685 | (2006.01) |
| C08G 63/91 | (2006.01) |

(52) U.S. Cl.
CPC .................. *A61K 47/34* (2013.01); *A61K 9/107* (2013.01); *A61K 9/1075* (2013.01); *A61K 9/19* (2013.01); *A61K 31/09* (2013.01); *A61K 31/337* (2013.01); *A61K 31/704* (2013.01); *A61K 47/42* (2013.01); *C08G 63/664* (2013.01); *C08G 63/6852* (2013.01); *C08G 63/823* (2013.01); *C08G 63/912* (2013.01); *C08G 64/183* (2013.01)

(58) Field of Classification Search
None
See application file for complete search history.

(56) References Cited

U.S. PATENT DOCUMENTS

| | | | |
|---|---|---|---|
| 7,217,770 | B2 | 5/2007 | Seo et al. |
| 2004/0197408 | A1 | 10/2004 | Gravett |
| 2010/0286075 | A1 | 11/2010 | Lee et al. |

FOREIGN PATENT DOCUMENTS

| | | |
|---|---|---|
| CN | 1429120 A | 7/2003 |
| CN | 1537636 A | 10/2004 |
| CN | 101265311 A | 9/2008 |
| CN | 101773465 A | 7/2010 |
| CN | 101787119 A | 7/2010 |
| CN | 103772686 A | 5/2014 |
| JP | 2007-056079 A | 3/2007 |
| JP | 2008-308423 A | 12/2008 |
| JP | 2009-102488 A | 5/2009 |
| JP | 2011-063562 A | 3/2011 |
| JP | 2011-509322 A | 3/2011 |
| JP | 2012-012606 A | 1/2012 |
| WO | WO 99/18142 A1 | 4/1999 |
| WO | WO 01/87345 A1 | 11/2001 |

OTHER PUBLICATIONS

Fan et al. Biomarcomolecules (2005), vol. 6, pp. 3051-3056.*

(Continued)

*Primary Examiner* — Patrick Lewis
(74) *Attorney, Agent, or Firm* — Howard & Howard Attorneys PLLC

(57) ABSTRACT

The present invention relates to a novel amphiphilic block copolymer and the preparation method thereof, as well as a micellar drug-loaded system formed by said copolymer and an anti-tumor drug. Said amphiphilic block copolymer comprises a hydrophilic segment and a hydrophobic segment, and the end group of said hydrophobic segment is end-capped with a hydrophobic group. Methoxypolyethylene glycol (or polyethylene glycol)-polyester block copolymer which has recognized safety is used as a fundamental material of the amphiphilic block copolymer of the present invention, and the terminal hydroxyl group of the polyester segment is modified with a hydrophobic group, whereby the compatibility between the drug molecule and the hydrophobic segments of the block copolymer is improved, and the interaction therebetween is enhanced. Moreover, a larger space for accommodating the drug molecules is provided. Said micelles are more effective in restricting the drug molecules inside the micellar core and preventing the drug from dissolved out of the micelles. Therefore, a drug-loaded micelle with high stability is obtained.

13 Claims, 8 Drawing Sheets

(56) References Cited

OTHER PUBLICATIONS

English language abstract for CN 1429120 extracted from espacenet.com database on Apr. 23, 2015, 1 page.

Machine-assisted English translation for CN 1537636 extracted from espacenet.com database on Apr. 23, 2015, 14 pages.

English language abstract and machine-assisted English translation for CN 101265311 extracted from espacenet.com database on Apr. 23, 2015, 13 pages.

English language abstract and machine-assisted English translation for CN 101773465 extracted from espacenet.com database on Apr. 24, 2015, 24 pages.

English language abstract and machine-assisted English translation for CN 101787119 extracted from espacenet.com database on Apr. 24, 2015, 24 pages.

Lee, SW et al., "Ionically Fixed Polymeric Nanoparticles As a Novel Drug Carrier", Pharmaceutical Research, vol. 24 No. 8 Aug. 2007, pp. 1508-1516.

Gaucher, G. et al. Polyester-Based Micelles and Nanoparticles for The Parenteral Delivery of Taxanes, Journal of Controlled Release 143 (2010) pp. 2-12.

Lee, SW et al., Development of Docetaxel-Loaded Intravenous Formulation Nanoxel-PM Using Polymer-Based Delivery System, Journal of Controlled Release 155 (2011) pp. 262-271.

Shao, C. et al., "In Vitro Stability of Paclitaxel and Docetaxel Binary-Drug Loaded Micelles", Journal of China Pharmaceutical University 2010, 41 (5) pp. 428-434, English Abstract only.

Huh K., et al. "Hydrotropic Polymer Micelle System for Delivery of Paclitaxel", Journal of Controlled Release 101 (2005) pp. 59-68.

International Search Report for Application No. PCT/CN2012/083958 dated Dec. 26, 2013, 7 pages.

English language abstract and machine-assisted English translation for CN 103772686 extracted from espacenet.com database on Apr. 30, 2015, 60 pages.

Liu, et al., "A mPEG-PLGA-b-PLL CoPolymer Carrier for Adriamycin and siRNA Delivery", Biomaterials 33 (2012), pp. 4403-4412.

Deng, Chao et al., "Synthesis and Characterization of Poly(ethylene glycol)-b-poly(L-lactide)-b-poly(L-glutamic acid) Triblock Copolymer", Polymer, vol. 46, No. 3, Jan. 26, 2005, pp. 653-659.

English language abstract and machine-assisted English translation for JP 2007-056079 extracted from espacenet.com database on Oct. 12, 2015, 18 pages.

English language abstract and machine-assisted English translation for JP 2008-308423 extracted from PAJ database on Oct. 12, 2015, 72 pages.

English language abstract and machine-assisted English translation for JP 2009-102488 extracted from PAJ database on Oct. 12, 2015, 64 pages.

English language abstract not found for JP 2011-509322; however, see English language equivalent U.S. 2010/0286075. Original document extracted from espacenet.com database on Oct. 12, 2015, 19 pages.

English language abstract and machine-assisted English translation for JP 2011-063562 extracted from espacenet.com database on Oct. 12, 2015, 24 pages.

English language abstract for JP 2012-012606 extracted from espacenet.com database on Oct. 12, 2015, 2 pages.

* cited by examiner

AMPHIPHILIC BLOCK COPOLYMER AND PREPARATION METHOD THEREOF AND MICELLAR DRUG-LOADING SYSTEM FORMED BY SAME WITH ANTITUMOR DRUG

RELATED APPLICATIONS

This application is the National Stage of International Patent Application No. PCT/CN2013/083958, filed on Sep. 22, 2013, which claims priority to and all the advantages of Chinese Patent Application No. 201210414318.5, filed on Oct. 26, 2012, the content of which is incorporated herein by reference.

TECHNICAL FIELD

The present invention relates to an amphiphilic block copolymer, the preparation method thereof, and a stable micellar drug-loaded system formed by said copolymer and an anti-tumor drug, and belongs to the field of nanodrug formulation.

BACKGROUND

Tumor is a disease which seriously threatens the life of human. It is great important to investigate and develop safe and effective anti-tumor drugs for improving the life quality of human.

Taxanes (including paclitaxel (PTX), docetaxel (DTX), cabazitaxel and larotaxel) are a class of very effective and broad-spectrum anti-tumor drugs. Its mechanism of action mainly includes polymerizing and stabilizing the microtubules, making the rapidly-divided tumor cells fixed on the stage of mitosis, blocking the replication of cancer cells and leading the cells death. It has been demonstrated in experiments in vitro that the taxanes had a significant radiosensitizing effect, and made the cells to suspend to G2 and M phases, during which the cells were sensitive to radiotherapy. However, almost all of the taxanes are highly hydrophobic and have low oral absorption, and the only route of administration thus far is injection. Because of the difficulty in preparing an aqueous solution of the taxanes, surfactants were often added in the commercially available formulations to increase the solubility of the drugs. However, there are many disadvantages for the solubilization method: (1) either polyoxyethylenated castor oil (Cremophor® EL) which is used as a solubilizer for paclitaxel (trade name: Taxol) or Tween 80 which is used as a solubilizer for docetaxel (trade name: Taxotere) and cabazitaxel (trade name: JEVTANA), easily causes allergy; therefore, patients need to accept anti-allergy treatment before using the drug; (2) the stability of the drug is poor, and the availability after injection is not high: drugs in the above formulations are easily precipitated upon diluting; the drugs must be subjected to a special filter before administration; the solution for injection has to be diluted slowly, and the precipitation degree of the drug often varies with different operators, which results in an inaccurate amount of drug injected into the body and then different therapeutic efficacy; (3) the hematologic toxicity is high: both of Cremophor® EL and Tween 80 can cause hematologic toxicity, which is the major factor restricting the improvement of the therapeutic dosage.

Doxorubicin is an anti-tumor antibiotic and belongs to cytotoxic drugs, like taxanes. It inhibits the synthesis of RNA and DNA, and has the strongest inhibition on RNA. It has a broad spectrum of anti-tumor and is effective to a variety of tumors. As a non-specific drug for cell cycle, doxorubicin can kill the tumor cells of various growth stages. Doxorubicin is mainly used in the treatment of acute leukemia, acute lymphoblastic leukemia and myeloid leukemia. Conventional formulations of Doxorubicin have side effects such as significant cardiac toxicity and bone marrow suppression.

Epirubicin, an isomer of Doxorubicin, has equal or slightly higher therapeutic efficacy and lower toxicity to heart, as compared with Doxorubicin.

Curcumin has received widespread attention in recent years as a non-cytotoxic drug with potential anti-tumor activity. The prominent feature of curcumin lies in that it has few side effect and has adjuvant therapeutic effects like anti-inflammatory, anti-oxidation, etc. The greatest drawback of curcumin is the low water solubility. Preparation of stable aqueous formulation of curcumin has attracted increasing attention in recent years.

Polymeric micelles have been developed as a novel drug delivery system in recent years. The micelles are usually formed by the orientation of a large amount of molecular chains on amphiphilic block copolymers. Drugs are encapsulated in the micellar core by weak interaction between the hydrophobic segment of the block copolymer and the drug molecules, and the hydrophilic segment is outward to stabilize the micelle, forming a typical core-shell structure. Polymeric micelles can not only increase the solubility of drugs and the therapeutic dosage, but also avoid the degradation and inactivation of drugs and reduce the toxicity by encapsulating the drugs therein. The diameter of the micelle is usually less than 100 nm, and the shell is usually segment of hydrophilic PEG; thus, they are able to avoid the phagocytosis of reticuloendothelial system (RES), increase the circulation time and achieve the passive targeting to tumors through EPR effect (enhanced permeability and retention effect). In addition, due to their high molecular weight, the polymeric micelles are able to avoid the renal clearance. Compared with small molecular surfactant, the CMC (critical micelle concentration) of polymeric micelle is much lower, and the micellar structure is maintained stable even upon dilution. The drug loading efficiency of the micellar drug-loaded system can reach 25%, which is able to fulfill the requirement of clinical dosage. At the same time, the polymeric materials are biodegradable and biocompatible.

Polymeric micelles are considered to be a novel drug delivery system with great potential, particularly for the anti-tumor drugs with poor solubility. However, their relatively low stability in solution has become the key problem for transferring this novel drug delivery system into clinical research. Particularly, the stability of taxane micelle is generally poor. The paclitaxel micelle for injection (trade name: Genexol PM) which is firstly approved in Korea, for example, keeps stable for no more than 24 h in solution at room temperature (Lee S W, et al, Ionically Fixed Polymeric Nanoparticles as a Novel Drug Carrier, Pharmaceutical Research, 2007, 24: 1508-1516). Samyang Corporation has made a great effort to improve the stability of paclitaxel micelles. For example, it was disclosed in CN01809632.8 that the terminal hydroxyl group of block copolymer was end-capped with acetoxy or benzoyl to increase the compatibility between the hydrophobic segment and the drug, and thus improving the stability of the micelle. However, the micelle prepared with the copolymer kept stable for just 3 days at room temperature in vitro, and the in vivo stability of the micelle was lower. The stability of micellar solution of docetaxel or cabazitaxel, which are the derivatives of paclitaxel, is even lower. Up to date, taking docetaxel micelle for example, there are few cases wherein it could be transferred to clinical study, and the key factor is the poor stability of the micelle solution (Gaucher G, et al. Polyester-based micelles and nanoparticles for the parenteral delivery of taxanes, Journal of Controlled Release, 2010, 143: 2-12). Taking Nanoxel PM™ micelle (wherein mPEG-PLA is used as the polymeric excipient, docetaxel is used as the drug) of Korea Samyang Corporation for instance, when the drug loading efficiency of the micelle is 5% and the drug concentration is 0.1-2 mg/ml, the micelle is stable at room temperature for only 6 h (Lee S W, et al, Development of docetaxel-loaded intravenous formulation, Nanoxel-PM™ using colymer-based delivery system, Journal of Controlled Release, 2011, 155: 262-271). The micelle disintegrates rapidly after been administrated to the body, and the drug immediately binds to the protein in blood (such as albumin); therefore, the EPR effect of the micelle is dismissed. The results of animal experiments showed that there is no difference in the drug efficacy between Nanoxel PM™ micelles and docetaxel injection, and there is no improvement in the most tolerated doses either; thus, there are no significant advantages of Nanoxel PM™ micelles. On the other hand, due to the structural similarity between docetaxel and cabazitaxel, the stability of cabazitaxel mPEG-PLA micelle is similar to that of docetaxel. It has been found in our study that when the drug concentration in mPEG-PLA/cabazitaxel micelle is 5 mg/mL, the micellar solution kept stable at room temperature for no longer than 2 h. Neither the in vivo efficacy nor the safety is improved effectively. In addition, there is large difficulty for the preparation of such unstable micelles in large-scale.

Taxanes are among the greatest discoveries in the research and development of anti-tumor drug in the last 20 years, and will remain as a main anti-tumor drug in the next 20 years. Due to its dose-limiting toxicity, the main focus for investigators has always been on fully utilizing the drug efficacy. As a great potential delivery system for taxanes, the instability of the micelles has become the biggest flaw of this drug delivery system, and the reasons causing such instability are still unclear. researchers have made great efforts to improve the stability of taxanes-encapsulated micelles. For example, as disclosed in the patent 201010001047, to improve the stability of paclitaxel micelle, amino acids were added to the micelle solution (the amino acids were added during the formation of the micelles), but in the disclosure there is no information about the location of amino acids in the micelles (only as a physical barrier agent of the micelle or co-present molecules with drug molecules in the hydrophobic core of the micelle). Meanwhile, as an auxiliary additive, it is unknown whether the amino acid is still able to maintain the micellar stability after administration to the body and dilution by blood; thus, the drug effect in vivo is still unclear. Moreover, it is reported that entrapping paclitaxel and docetaxel together in a copolymer micelle can significantly increase the drug loading efficiency and the stability of the micelle; but this binary-drug loaded micelle has not been recognized in clinical yet (Shao Cheng Wei, etc., In vitro stability of paclitaxel and docetaxel binary-drug loaded micelles, Journal of China Pharmaceutical University, 2010, 41:428-434). Huh et al synthesized a micelle with the block copolymer of PDENA-PEG. The micelle showed long-term stability after encapsulating paclitaxel, but the insufficient data supporting safety of the polymer materials present great security challenges for clinical use (Huh K M, et al. Hydmtropic polymer micelle system for delivery of paclitaxel. Journal of Controlled Release, 2005, 101 (1-3):59-68).

SUMMARY OF THE INVENTION

The objective of the present invention is to provide an amphiphilic block copolymer to address the above problems in the prior art. Methoxypolyethylene glycol (or polyethylene glycol)-polyester block copolymer which has recognized safety is used as a fundamental material of the amphiphilic block copolymer of the present invention, and the terminal hydroxyl group of the polyester segment is modified with a hydrophobic group by introduction of a hydrophobic group with a large spatial structure, such as t-butoxycarbonyl group, amino acids with phenyl or derivatives thereof, whereby the compatibility between the drug molecule and the hydrophobic segment of the block copolymer is improved and the interaction therebetween is enhanced; the introduction of a hydrophobic group with a large spatial structure provides a larger space for drug molecules entering the micelles core; thus, it is more difficult for the drugs to dissolve out of the micelle core, and thus a drug-loaded micelle with high stability is obtained. The greatest significance of the present invention lies in that the stability of the micelle in solution is improved, especially the stability in vivo; thus, ensuring EPR effect of the micelles, achieves better bioavailability and therapeutic effect of the drugs.

The technical solutions of the present invention are provided as follows.

An amphiphilic block copolymer, characterized in that the hydrophilic segment thereof is polyethylene glycol (PEG) or methoxypolyethylene glycol (mPEG) with the number-average molecular weight in the range of 400 to 20000; the hydrophobic segment thereof is selected from the group consisting of polylactide (PLA), polyglycolide (PGA), poly(lactic-co-glycolic acid) (PLGA), polycaprolactone (PCL), polycarbonate (PTMC) and derivatives thereof, and polydioxanone (PPDO) and derivatives thereof, each has a number-average molecular weight in the range of 500 to 100000 and is end-capped with a hydrophobic group selected from the group consisting of t-butyl acyl, t-butyl acetyl, an amino acid residue and an amino acid derivative residue.

In a preferred embodiment, said amino acid derivative is preferably selected from γ-benzyl glutamic acid, β-benzyl aspartic acid and amino-protected amino acid derivative.

In a preferred embodiment, said amino acid derivative is further preferably selected from an amino acid protected with benzyl or t-butoxycarbonyl (Boc).

In a preferred embodiment, said amino acid derivative is preferably t-butoxycarbonyl phenylalanine.

In the present invention, said hydrophobic segment is preferably selected from the group consisting of polylactide (PLA), polyglycolide (PGA), poly(lactic-co-glycolic acid) (PLGA), polycaprolactone (PCL), polycarbonate (PTMC) and derivatives thereof, and polydioxanone (PPDO) and derivatives thereof, each has a number-average molecular weight in the range of 1,000 to 50,000; said hydrophilic segment is preferably selected from polyethylene glycol and methoxypolyethylene glycol with a number-average molecular weight in the range of 750 to 5,000.

Another objective of the present invention is to provide a method for preparing said amphiphilic block copolymer.

The technical solutions provided by the present invention are described as follows:

The method for preparing said amphiphilic block copolymer comprises the steps below:

1) adding a hydrophilic segment with a number-average molecular weight in the range of 400 to 20000 to a flask for polymerization; heating to 100 □-130 □ and dehydrating under vacuum for 2 h-4 h; then adding the monomer of the hydrophobic segment and stannous octoate as the catalyst, wherein the weight of stannous octoate is 0.3‰-1‰ of said monomer; sealing the flask under vacuum, carrying out reaction with the above reactants at 100 □-150 □ for 12 h-24 h;

then dissolving with dichloromethane, ethanol, tetrahydrofuran, methanol, ethyl acetate or acetone; adding diethyl ether to thoroughly precipitate the polymer, followed with filtration and drying under vacuum to obtain the block copolymer composed of the hydrophilic segment and the hydrophobic segment, wherein said hydrophilic segment is polyethylene glycol (PEG) or methoxypolyethylene glycol (mPEG);

2) dissolving the block copolymer composed of the hydrophilic segment and the hydrophobic segment in ethyl acetate, tetrahydrofuran, dichloromethane, ethyl acetate or double distilled water; then adding t-butyl acyl, t-butyl acetyl, amino acid residue or amino acid derivative residue to carry out the reaction for converting the terminal hydroxyl group into a hydrophobic group; filtrating to remove the insoluble substance, adding sufficient amount of diethyl ether to precipitate the polymer; filtrating and drying under vacuum to obtain the target copolymer.

Another objective of the present invention is to provide a micellar drug-loaded system formed by said amphiphilic block copolymer with an antitumor drug.

The technical solutions of the present invention are provided as follows:

The micellar drug-loaded system formed by said amphiphilic block copolymer with an anti-tumor drug, wherein said micellar drug-loaded system comprises at least one said amphiphilic block copolymer, at least one anti-tumor drug with a therapeutically effective amount, and a pharmaceutically acceptable pharmaceutical auxiliary agent.

In a preferred embodiment, said pharmaceutical auxiliary agent is excipient for lyophilization.

In a preferred embodiment, said excipient for lyophilization is at least one of lactose, mannitol, sucrose, trehalose, fructose, glucose, sodium alginate and gelatin.

Said pharmaceutical auxiliary agent further include an antioxidant, metal ion complexing agent, pH adjusting agent or isotonicity adjusting agent, and the like; said antioxidant is sodium sulfite, sodium bisulfite or sodium metabisulfite, and the like; said metal ion complexing agent is edetate disodium, calcium disodium edetate or sodium cyclohexylenediamine tetraacetate, and the like; said pH adjusting agent is citric acid, sodium bicarbonate, disodium hydrogen phosphate or sodium dihydrogen phosphate, and the like; said isotonicity adjusting agent is sodium chloride or glucose, and the like.

In a preferred embodiment, said anti-tumor drug is at least one of taxanes, including paclitaxel (PTX), docetaxel (DTX), cabazitaxel and larotaxel, curcumin, doxorubicin, epirubicin and the like.

In a preferred embodiment, the weight ratio of the amphiphilic block copolymer to the drug is in the range of 99.5:0.5 to 50:50, preferably in the range of 99:1 to 75:25.

In a preferred embodiment, said excipient for lyophilization accounts for 0 to 99.9%, preferably 10.0% to 80.0%, of the entire system by weight.

The anti-tumor drug-polymer micellar formulation in the present invention can be used in the treatment of a cancer, preferably selected from the group consisting of breast cancer, prostatic cancer, ovarian cancer, intestinal cancer, lung cancer, liver cancer, head and neck cancer, etc.

The therapeutically effective amount as mentioned in the present invention refers to the amount of anti-tumor drug contained in said micellar drug-loading system is effective in the treatment of cancers (particularly, breast cancer, prostatic cancer, ovarian cancer, intestinal cancer, lung cancer, liver cancer, head and neck cancer, etc.).

The micellar drug-loaded system of the present invention may be administered by injection, and is generally prepared as lyophilized powder. Additionally, a skilled person in the art may determine the administration dosage by reference to the dosage of existing anti-tumor drugs, and adjust it according to the individual condition.

The present invention also provides a method for preparing said micellar drug-loading system formed by the amphiphilic block copolymer and an anti-tumor drug, including a dialysis method, a direct dissolution method, a film hydration method, a solid dispersion method and a high-energy homo-emulsification method, preferably a film hydration method and a solid dispersion method.

The steps of said film hydration method includes: dissolving the polymer and the drug in organic solvent; removing the solvent by rotary evaporation; then adding water for injection to dissolve the drug film so as to get the solution of the drug-loaded micelle; and obtaining the lyophilized powder of the micelle after sterilization by filtration and lyophilization.

The steps of said solid dispersion method includes: dissolving the drug in the polymer which is in the molten state upon heating to give a clear mixture (during this step, a small amount of organic solvent may be added to help the dissolution); adding water for injection to dissolve and get the solution of the micelle; and obtaining the lyophilized powder of the micelle after sterilization by filtration and lyophilization.

As compared with the prior art, the present invention has the following properties.

1) In the present invention, in view of the hydrophobicity and large steric structure of most anti-tumor drugs, the terminal hydroxyl group of the polyester segment is modified with a hydrophobic group, whereby the compatibility between drug molecules and the hydrophobic segment of the block copolymer is improved, and the interaction therebetween is increased. Meanwhile, the space for accommodating the drug molecules in the micellar core is increased, and the drug molecules are restricted in the micellar core, and are difficult to be dissolved out of the micelle core. Thus, a series of drug-loaded micelles with high stability both in vivo and in vitro are obtained. Said drug-loaded micelles can be prepared as lyophilized formulations.

2) It is demonstrated in the experiments that the lyophilized formulation of the anti-tumor drug-loaded micelle prepared by the amphiphilic block copolymer of the present invention dispersed rapidly to form a clear solution with bluish opalescence after reconstitution. The solution is stable at room temperature for at least 24 hours without obvious precipitation of drugs, and provides potential EPR effect in vivo after injection. The invention has good prospects for industrial applications.

EMBODIMENTS

For better understanding of the present invention, the following examples are provided to further interpret the present invention. However, the examples are not intended to limit the present invention in any ways.

Example 1

Preparation of Amphiphilic Block Copolymers (1) Synthesis of methoxy poly(ethylene glycol)-poly(lactic-co-glycolic acid) block copolymer end-capped with t-butyl acyl (mPEG$_{2000}$-PLGA$_{2000}$-TB)

18.2 g of mPEG (number-average molecular weight of 2,000) was added to a flask for polymerization, heated to 100° C. and dehydrated under vacuum for 3 h. Then 26 mg of stannous octoate, 11.6 g of glycolide (GA) and 14.4 g of D, L-lactide (D, L-LA) were added. The flask was sealed under vacuum and the polymerization was conducted at 130° C. for 15 h. The reactants were dissolved in dichloromethane, and added with a large amount of diethyl ether to thoroughly precipitate the polymer. After filtration and drying under vacuum, mPEG$_{2000}$-PLGA$_{2000}$ block copolymer was obtained.

4 g of mPEG$_{2000}$-PLGA$_{2000}$ was dissolved in 20 ml of dichloromethane, and 0.5 g of potassium carbonate was added, and 0.25 g of pivaloyl chloride was added under stirring. The reaction was conducted at room temperature for 24 h. The insoluble substance was removed by filtration. A large amount of diethyl ether was added to thoroughly precipitate the polymer. After filtrated and drying under vacuum, mPEG$_{2000}$-PLGA$_{2000}$-TB was obtained.

Note: TB is an abbreviation for t-butyl acyl.

Figure 1:
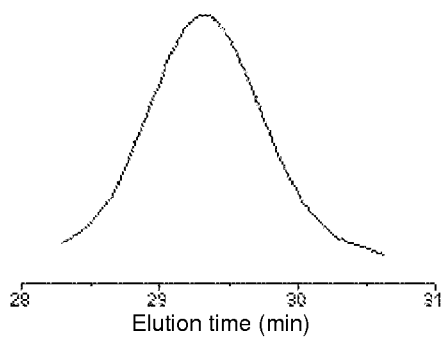
FIG. 1 is the gel permeation chromatogram of $mPEG_{2000}$-$PLGA_{2000}$-TB, PDI=1.05.

The gel permeation chromatogram of mPEG$_{2000}$-PLGA$_{2000}$-TB was shown in FIG. 1, wherein the PDI is 1.05;

With Deuterated chloroform as solvent, 400MBruker NMR equipment was used to characterize the polymer structure, and $^1$H NMR data of mPEG$_{2000}$-PLGA$_{2000}$-TB were shown as follows:

$^1$H NMR (CDCl$_3$) δ (1.56 ppm, (CH$_3$)$_3$C, CHCH$_3$O), δ (3.55-3.75 ppm, 4H, CH$_2$CH$_2$O), δ (5.15-5.23 ppm, 1H, CHCH$_3$O).

(2) Synthesis of methoxy poly(ethylene glycol)-polylactide block copolymer end-capped with t-butoxycarbonyl phenylalanine residue (mPEG$_{2000}$-PLA$_{1800}$-BP)

20 g of mPEG (number-average molecular weight of 2,000) was added to a flask for polymerization, heated to 120° C., and dehydrated under vacuum for 3 h. 25 mg of stannous octoate and 25 g of D, L-lactide (D, L-LA) were added. The reaction flask was sealed under vacuum. The polymerization was conducted at 130° C. for 12 h and the reactants were dissolved in ethanol. A large amount of diethyl ether was added to thoroughly precipitate the polymer. After filtration and drying under vacuum, mPEG$_{2000}$-PLA$_{1800}$ block copolymer was obtained.

6.65 g of Boc-L-phenylalanine was dissolved in 50 ml of anhydrous ethyl acetate and 4.2 ml of triethylamine was added. The above solution was cooled to −10° C. and 3.66 ml of pivaloyl chloride was added. The reaction was conducted under stirring at 0° C. for 2 h and then at room temperature for another 1 h. The insoluble substance was removed by filtration and the solvent was removed under vacuum, thus obtaining a viscous liquid.

25 ml of dichloromethane was added for dissolution. The obtained solution was added to 75 ml of dichloromethane solution containing 15 g of mPEG$_{2000}$-PLA$_{1800}$. After thorough mixing, 14 ml of pyridine and 160 mg of tetramethyl aminopyridine were added. The mixture was reacted at 0° C. for 2 h and then at room temperature for another 24 h. After filtration and removal of solvent, the obtained polymer was redissolved in 100 ml of ethanol and cooled at −20° C. for 1 h. After filtration and drying under vacuum, mPEG$_{2000}$-PLA$_{1800}$-BP was obtained.

Note: BP is an abbreviation for t-butoxycarbonyl phenylalanine residue.

Figure 2:
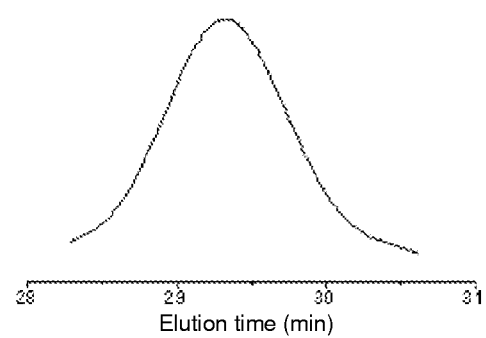
FIG. 2 is the gel permeation chromatogram of $mPEG_{2000}$-$PLA_{1800}$-BP, PDI=1.05.
Figure 3:
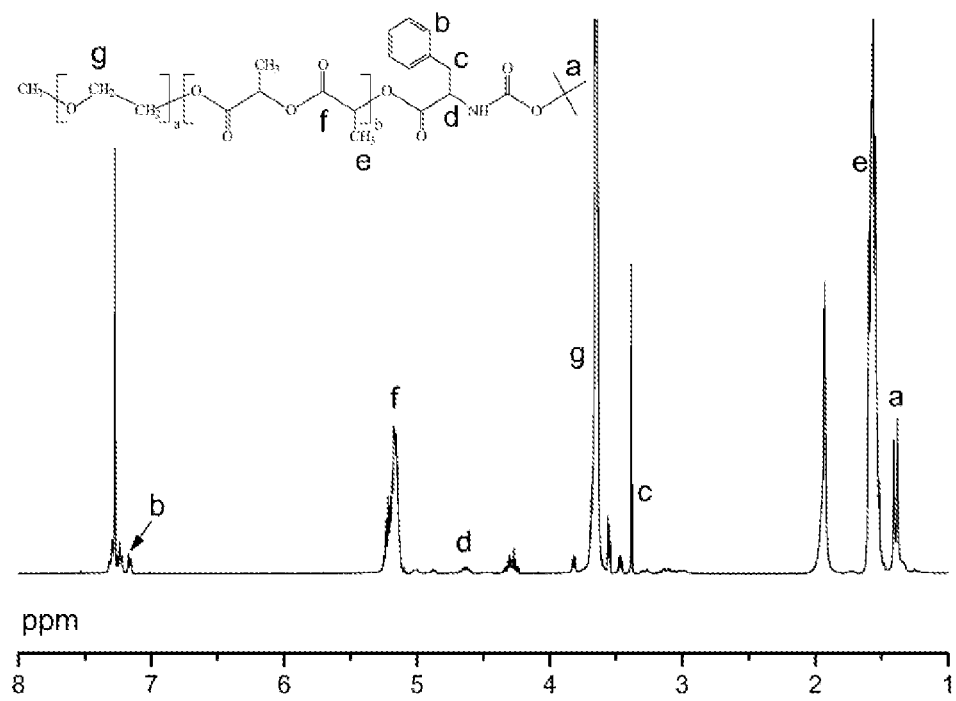
FIG. 3 is the $^1$H-NMR spectra of $mPEG_{2000}$-$PLA_{1800}$-BP.

The gel permeation chromatogram of mPEG$_{2000}$-PLA$_{1800}$-BP was shown in FIG. 2, wherein the PDI is 1.05;

With Deuterated chloroform as solvent, 400MBruker NMR equipment was used for characterization of the polymer structure. The $^1$H NMR spectrum of mPEG$_{2000}$-PLA$_{1800}$-BP was shown in FIG. 3, and the $^1$H NMR data were as follows:

$^1$H NMR (CDCl$_3$) δ (1.38-1.41 ppm, 9H, (CH$_3$)$_3$C,), δ (1.51-1.60 ppm, 3H, CHCH$_3$O), δ (3.38 ppm, 2H, CH$_2$C$_6$H$_5$), δ (3.63-3.70 ppm, 4H, CH$_2$CH$_2$O), δ (4.60-4.66 ppm, 1H, CHCH$_2$C$_6$H$_5$), 6 (5.15-5.17 ppm, 1H, CHCH$_3$O).

(3) Synthesis of methoxy poly(ethylene glycol)-polylactide block copolymer end-capped with β-benzyl-aspartic acid residue (mPEG$_{2000}$-PLA$_{1800}$-Asp)

The synthesis of mPEG$_{2000}$-PLA$_{1800}$ was the same as Example 1 (2).

100 ml of deionized water and 100 ml of dioxane (as a mixed solvent) were added to 22.3 g of benzyl L-aspartate and stirred, then 30 ml of 4N NaOH was added and stirred until the benzyl ester was dissolved. The reaction flask was cooled in an ice bath and the temperature was controlled below 4° C. Separately, 8.7 ml of bromoacetyl bromide was dissolved in 35 ml of refined dioxane and about 25 ml of 4N NaOH. Under vigorous stirring, the two solutions were simultaneously and dropwisely added together through two dropping funnels. The pH value was controlled between 8 and 9 (it took about 30 min for the addition). After the addition was completed, the reaction was continued for 5 min and the pH value was adjusted to 2 using concentrated hydrochloric acid. 200 ml of diethyl ether was used for extraction. The mixture was contained in the organic layer. The organic layer was washed with saturated NaCl solution for 5 times. Finally, anhydrous magnesium sulfate was added to the organic layer for drying for 48 h. A yellow viscous oil was obtained by concentration under vacuum, and was placed in a Petri dish to obtain 25 g of bromoacetyl benzyl L-aspartate as a crystal.

10 g of $mPEG_{2000}$-$PLA_{1800}$ was dissolved in 50 ml of dichloromethane, and 5 ml of triethylamine and 2.5 g of bromoacetyl benzyl L-aspartate were added. The reactants were stirred at room temperature for 24 h, precipitated with diethyl ether and dried under vacuum to give $mPEG_{2000}$-$PLA_{1800}$-Asp.

Note: Asp is an abbreviation for benzyl aspartic acid residue.

Figure 4:
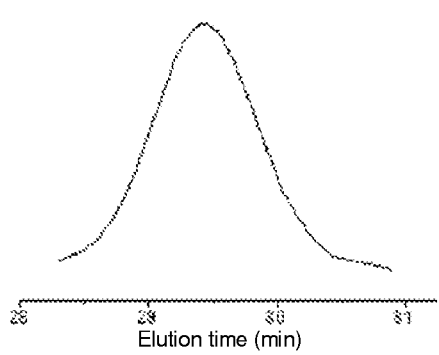
FIG. 4 is the gel permeation chromatogram of $mPEG_{2000}$-$PLA_{1800}$-Asp, PDI=1.05.

The gel permeation chromatogram of $mPEG_{2000}$-$PLA_{1800}$-Asp was shown in FIG. 4, wherein the PDI is 1.05.

With Deuterated chloroform as solvent, 400MBruker NMR was used to characterize the polymer structure. The $^1H$ NMR data of $mPEG_{2000}$-$PLA_{1800}$-Asp were shown as follows:

$^1H$ NMR (CDCl$_3$) δ (1.51-1.60 ppm, 3H, CHCH$_3$O), δ (2.90-3.15 ppm, 2H, OCOCH$_2$), δ (3.63-3.70 ppm, 4H, CH$_2$CH$_2$O), δ (5.13-5.15 ppm, 2H, CH$_2$C$_6$H$_5$), δ (5.15-5.17 ppm, 1H, CHCH$_3$O), δ (7.34 ppm, 5H, C$_6$H$_5$).

(4) Synthesis of methoxyl poly(ethylene glycol)-poly(lactic-co-glycolic acid) block copolymer end-capped with tyrosine residue ($mPEG_{2000}$-$PLGA_{2000}$-TS)

The synthesis of $mPEG_{2000}$-$PLGA_{2000}$ was the same as Example 1 (1).

10 g of $mPEG_{2000}$-$PLGA_{2000}$ was dissolved in 200 ml of double distilled water, then 1.91 g of 1-ethyl-(3-dimethylaminopropyl) carbodiimide hydrochloride and 1.8 g of tyrosine were added. After the reaction was conducted at room temperature for 48 h, the product was extracted three times with 200 ml of dichloromethane. The combined organic layer was washed with saturated brine for five times, dried over anhydrous magnesium sulfate and precipitated with diethyl ether. After drying under vacuum, $mPEG_{2000}$-$PLGA_{2000}$-TS was obtained.

Note: TS is an abbreviation for tyrosine residue.

Figure 5:
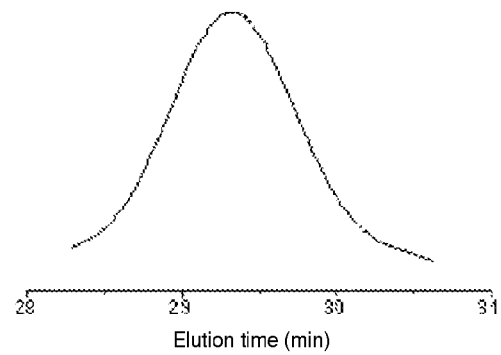
FIG. 5 is the gel permeation chromatogram of $mPEG_{2000}$-$PLGA_{2000}$-TS, PDI=1.05.

The gel permeation chromatogram of $mPEG_{2000}$-$PLGA_{2000}$-TS was shown in FIG. 5, wherein the PDI is 1.05.

With Deuterated chloroform as solvent, 400MBruker NMR equipment was used to characterize the polymer structure. $^1H$ NMR data of $mPEG_{2000}$-$PLGA_{2000}$-TS were shown as follows:

$^1H$ NMR (CDCl$_3$) δ (1.51-1.60 ppm, 3H, CHCH$_3$O), δ (2.94-3.00 ppm, 2H, CH$_2$C$_6$H$_5$), δ (3.63-3.70 ppm, 4H, CH$_2$CH$_2$O), δ (5.15-5.17 ppm, 1H, CHCH$_3$O), δ (6.74-6.93 ppm, 5H, C$_6$H$_5$).

(5) Synthesis of poly(ethylene glycol)-poly(lactic-co-glycolic acid) block copolymer end-capped with tyrosine residue ($PEG_{2000}$-$PLGA_{2000}$-TS)

The synthetic method of $PEG_{2000}$-$PLGA_{2000}$ was as described in Example 1 (1).

10 g of $PEG_{2000}$-$PLGA_{2000}$ was dissolved in 200 ml of double distilled water, then 1.91 g of 1-ethyl-(3-dimethylaminopropyl) carbodiimide hydrochloride and 1.8 g of tyrosine were added. After the reaction was conducted at room temperature for 48 h, the product was extracted three times with 200 ml of dichloromethane. The combined organic phase was washed with saturated brine for five times, dried over anhydrous magnesium sulfate and precipitated in diethyl ether. After drying under vacuum, $PEG_{2000}$-$PLGA_{2000}$-TS was obtained.

Note: TS is an abbreviation for tyrosine residue.

Figure 6:
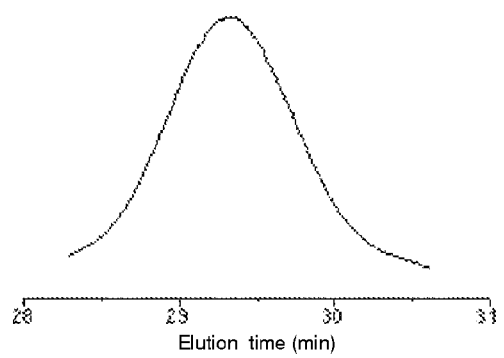
FIG. 6 is the gel permeation chromatogram of $PEG_{2000}$-$PLGA_{2000}$-TS, PDI=1.05.

The gel permeation chromatogram of $PEG_{2000}$-$PLGA_{2000}$-TS was shown in FIG. 6, wherein the PDI is 1.05.

With Deuterated chloroform as solvent, 400MBruker NMR was used to characterize the polymer structure. The $^1H$ NMR data of $PEG_{2000}$-$PLGA_{2000}$-TS were shown as follows:

$^1H$ NMR (CDCl$_3$) δ (1.51-1.60 ppm, 3H, CHCH$_3$O), δ (2.94-3.00 ppm, 2H, CH$_2$C$_6$H$_5$), δ (3.63-3.70 ppm, 4H, CH$_2$CH$_2$O), δ (5.15-5.17 ppm, 1H, CHCH$_3$O), δ (6.74-6.93 ppm, 5H, C$_6$H$_5$).

(6) Synthesis of methoxyl poly(ethylene glycol)-polycaprolactone block copolymer end-capped with t-butoxycarbonyl phenylalanine residue ($mPEG_{5000}$-$PCL_{4000}$-BP)

20 g of mPEG (number-average molecular weight of 5,000) was added to a flask for polymerization, heated to 130° C. and dehydrated under vacuum for 4 h. 20 mg of stannous octoate and 20 g of caprolactone (CL) were added. After the reaction flask was sealed under vacuum, the above reactants were reacted at 130° C. for 24 h, dissolved in dichloromethane and thoroughly precipitated by addition of a large amount of diethyl ether. After filtration and vacuum drying, $mPEG_{5000}$-$PCL_{4000}$ block copolymer was obtained.

6.65 g of Boc-L-phenylalanine was dissolved in 50 ml of anhydrous ethyl acetate, and 4.2 ml of triethylamine was added. The above solution was cooled to −10 □ and 3.66 ml of pivaloyl chloride was added. The reaction was conducted under stirring at 0 □ for 2 h and then at room temperature for another 1 h. The insoluble substance was removed by filtration and the solvent was removed under vacuum to obtain a viscous liquid.

25 ml of dichloromethane was added for dissolution. The obtained solution was added to 150 ml of dichloromethane solution containing 30 g of $mPEG_{2000}$-$PLA_{1800}$ and thoroughly mixed. 14 ml of pyridine and 160 mg of tetramethyl aminopyridine were added. The mixture was reacted at 0 □ for 2 h and then at room temperature for another 24 h. After filtration, the polymer solution was precipitated in diethyl ether of −20 □ and dried under vacuum, to give $mPEG_{5000}$-$PCL_{4000}$-BP.

Note: BP is an abbreviation for t-butoxycarbonyl phenylalanine residue.

Figure 7:
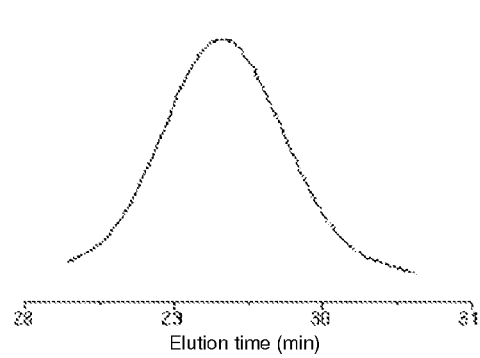
FIG. 7 is the gel permeation chromatogram of $mPEG_{5000}$-$PCL_{4000}$-BP, PDI=1.07.
Figure 8:
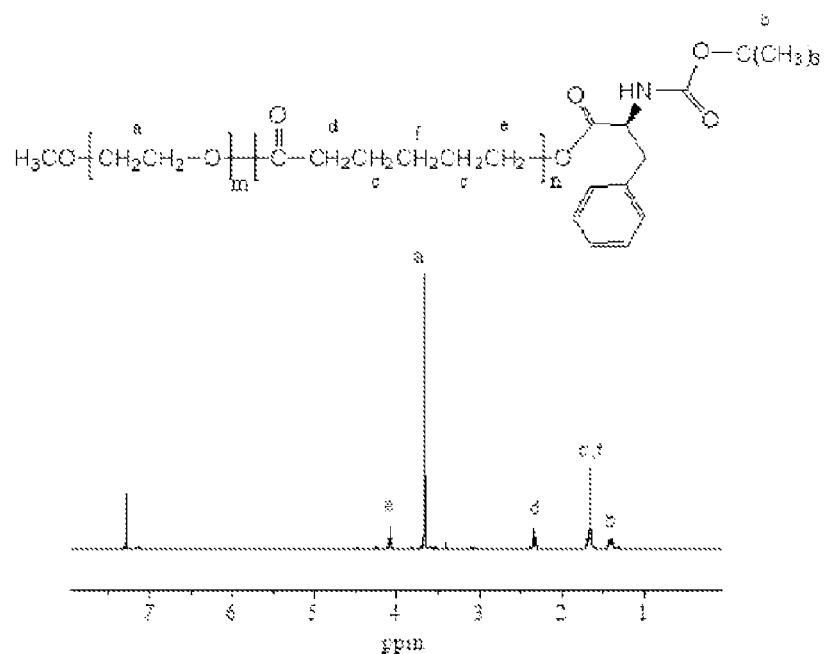
FIG. 8 is the $^1$H-NMR spectra of $mPEG_{5000}$-$PCL_{4000}$-BP.

The gel permeation chromatogram of $mPEG_{5000}$-$PCL_{4000}$-BP was shown in FIG. 7, wherein the PDI is 1.08;

With Deuterated chloroform as solvent, 400MBruker NMR was used to characterize the polymer structure. The $^1H$ NMR spectrum of $mPEG_{2000}$-$PLA_{1800}$-BP was shown in FIG. 8, and the $^1H$ NMR data were shown as follows:

$^1H$ NMR (CDCl$_3$) δ (1.38-1.43 ppm, 9H, (CH$_3$)$_3$C,), δ (1.53-1.64 ppm, 4H, CH$_2$CH$_2$CH$_2$), δ (2.34 ppm, 2H, COCH$_2$CH$_2$), δ (3.63-3.70 ppm, 4H, CH$_2$CH$_2$O), δ (4.06-4.15 ppm, 2H, OCH$_2$CH$_2$).

Example 2

Figure 9:
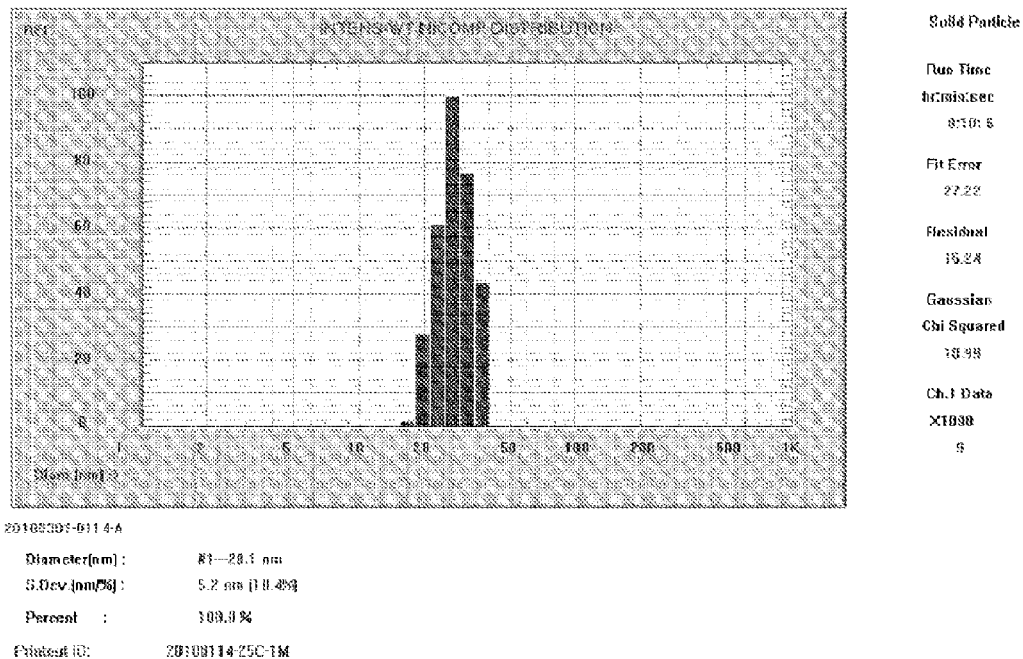
FIG. 9 is a figure showing size distribution of $mPEG_{5000}$-$PCL_{4000}$-BP/paclitaxel micelle.

Preparation of Lyophilized Formulation of Anti-Tumor Drug-Loaded Polymeric Micelles (1) Preparation of $mPEG_{5000}$-$PCL_{4000}$-BP/paclitaxel micelle and the lyophilized formulation thereof 150 mg of $mPEG_{5000}$-$PCL_{4000}$-BP as prepared in Example 1 and 30 mg of paclitaxel were dissolved in 2 ml of tetrahydrofuran. 5 ml of ultrapure water was added dropwisely under stirring. After addition, the solution was stirred at room temperature overnight, and then the organic solvent was removed to obtain a clear solution of paclitaxel micelle with obvious blue opalescence. 120 mg of mannitol was added, and the obtained solution was sterilized through a 0.22 μm membrane filter and lyophilized to obtain the lyophilized powder of paclitaxel micelle. By analysis with LC-MS/MS, the drug encapsulation efficiency of the paclitaxel micelle was 98.6%, and the drug loading efficiency was greater than 11.2%. The results of particle diameter measurement were shown in FIG. 9. The average particle diameter of the micelle was 33.8 nm, and the polydispersity index (PDI) was 0.1.

The lyophilized powder was reconstituted in saline to obtain a solution of 5 mg/mL. The solution kept stable at room temperature for more than 7 days, which was significantly longer than that of the micell of polymer end-capped with acetoxyl or benzoyl.

Figure 10:
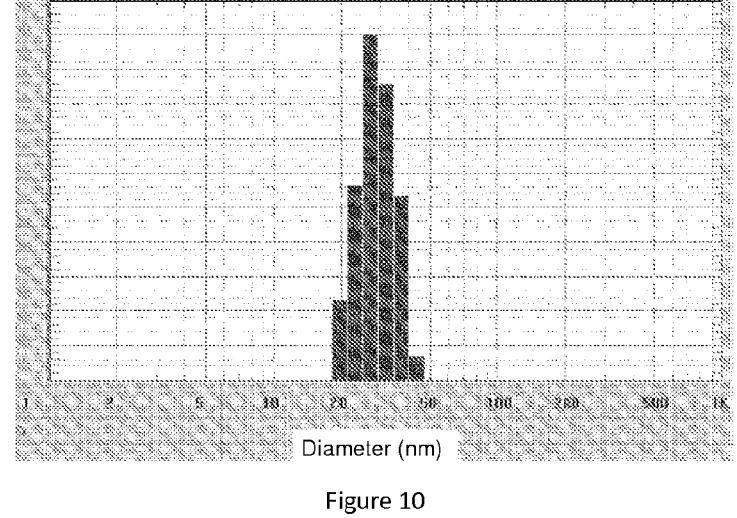
FIG. 10 is a figure showing size distribution of mPEG$_{2000}$-PLA$_{1800}$-BP/docetaxel micelle.

(2) Preparation of $mPEG_{2000}$-$PLA_{1800}$-BP/docetaxel micelle and the lyophilized formulation thereof 100 mg of docetaxel and 1.9 g of $mPEG_{2000}$-$PLA_{1800}$-BP as prepared in Example 1 were dissolved in 25 ml of anhydrous ethanol. The organic solvent was removed at 45 □ by rotary evaporation and 25 ml of saline was added to dissolve the drug-contained thin film. 400 mg of lactose was added and then the solution was sterilized through a 0.22 μm membrane filter and lyophilized to obtain the lyophilized powder of docetaxel micelle. It was showed by LC-MS/MS analysis that the drug encapsulation efficiency of the micelle was 95.8%, the drug loading efficiency was 4.76%. The results of particle diameter measurement were shown in FIG. 10. The average particle diameter was 23.3 nm, and the polydispersity index (PDI) was 0.02.

The lyophilized powder was reconstituted in saline to obtain a solution of 5 mg/mL, stored at room temperature for 90 days, and the content of dissolved docetaxel in the solution was higher than 90%.

Figure 11:
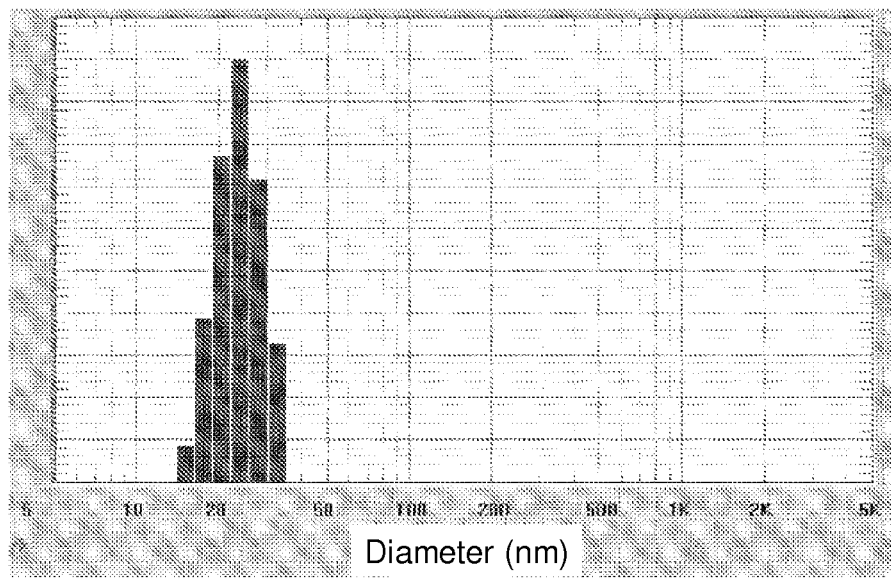
FIG. 11 is a figure showing size distribution of mPEG$_{2000}$-PLGA$_{2000}$-TB/cabazitaxel micelle.

(3) Preparation of $mPEG_{2000}$-$PLGA_{2000}$-TB/cabazitaxel micelles and the lyophilized formulation thereof 1.9 g of $mPEG_{2000}$-$PLGA_{2000}$-TB, as prepared in Example 1, was heated to 50 □ until melted. 100 mg of cabazitaxel was added and dissolved in the molten polymer under stirring to give a clear and transparent mixture, then 25 ml of 50□ saline was added to dissolve the mixture of polymer/drug to obtain the micellar solution. 400 mg of sucrose was added and the solution was sterilized by filtration through a 0.22 μm membrane filter and lyophilized to obtain the lyophilized powder of cabazitaxel micelle. It was shown by LC-MS/MS analysis that the drug encapsulation efficiency was 96.2% and the drug loading efficiency was greater than 4.82%. The results of particle diameter measurement were shown in FIG. 11. The average particle diameter was 24.2 nm, and the polydispersity index (PDI) was 0.02.

Said lyophilized powder was reconstituted in saline to obtain a solution of 5 mg/mL and stored at room temperature for 90 days. The content of dissolved cabazitaxel in the solution was higher than 90%.

(4) Preparation of $mPEG_{2000}$-$PLA_{1800}$-BP/curcumin and the lyophilized formulation thereof 100 mg of curcumin and 1.9 g of $mPEG_{2000}$-$PLA_{1800}$-BP as prepared in Example 1 were dissolved in 25 ml of anhydrous ethanol. The organic solvent was removed at 50 □ by rotary evaporation. 25 ml of saline was added to dissolve the drug-contained thin film. 400 mg of sodium alginate was added and the solution was sterilized through a 0.22 μm membrane filter and lyophilized to obtain the lyophilized powder of curcumin micelle. It was shown by LC-MS/MS analysis that the drug encapsulation efficiency was 98.9% and the drug loading efficiency was 4.88%. The average particle diameter was 15.3 nm, and the polydispersity index (PDI) was 0.02.

Said lyophilized powder was reconstituted in saline to obtain a solution of 5 mg/mL and stored at room temperature for 7 days. The content of dissolved curcumin in the solution was more than 90%.

(5) Preparation of $mPEG_{2000}$-$PLGA_{2000}$-TB/doxorubicin and the lyophilized formulation thereof 300 mg of $mPEG_{2000}$-$PLGA_{2000}$-TB as prepared in Example 1 and 40 mg of doxorubicin hydrochloride were dissolved in chloroform at 40 □. 0.1 ml of triethylamine was added and stirred at room temperature for 1 h. The organic solvent was removed by rotary evaporation and 50 ml of 10 mM HBS buffer was added to dissolve the drug-contained thin film. The triethylamine hydrochloride was removed by dialysis or ultrafiltration, then 250 mg of gelatin was added. The solution was sterilized through a 0.22 μm membrane filter and lyophilized to obtain the lyophilized powder of doxorubicin micelle. It was shown by LC-MS/MS analysis that the drug encapsulation efficiency was 94.7% and the drug loading efficiency was more than 22.47%. The average particle diameter was 19.4 nm, and the polydispersity index (PDI) was 0.04.

Said lyophilized powder was reconstituted in saline to obtain a solution of 2 mg/mL and stored at room temperature for 24 h. The content of dissolved doxorubicin in the solution was higher than 90%.

Example 3

Stability Test (1) Stability test of $mPEG_{2000}$-$PLA_{1800}$-BP/docetaxel micelle The lyophilized powder of $mPEG_{2000}$-$PLA_{1800}$-BP/docetaxel micelle was reconstituted (docetaxel concentration: 6 mg/ml) and stored in an incubator at 25 □ for a certain period. After centrifugation at 10,000 rpm for 10 min, the drug content in the supernatant was measured by HPLC.

Figure 12:
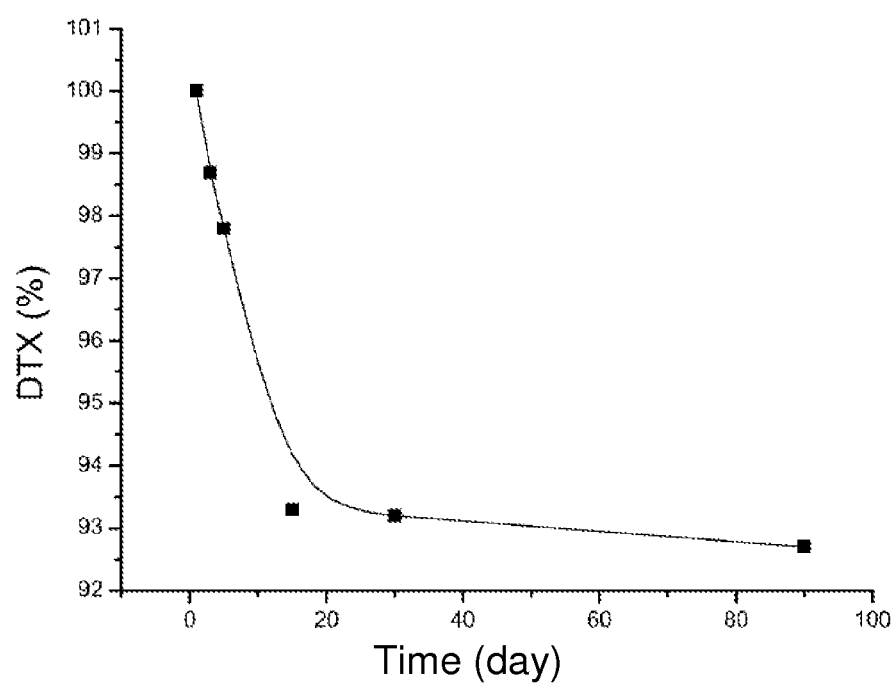
FIG. 12 shows results of the stability test of mPEG$_{2000}$-PLA$_{1800}$-BP/docetaxel micellar solution.

The content variation with time of the drug in a dissolved state was shown in FIG. 12. The content of the dissolved drug in the solution of $mPEG_{2000}$-$PLA_{1800}$-BP/docetaxel micelle was decreased to some extent within the initial 15 days. Later, the release of the drug was much slower. The content of the drug in a dissolved state remained above 90% even over 90 days.

(2) Stability test of $mPEG_{2000}$-$PLGA_{2000}$-TB/cabazitaxel micelle

The lyophilized powder of $mPEG_{2000}$-$PLGA_{2000}$-TB/cabazitaxel micelle was reconstituted (cabazitaxel concentration: 6 mg/ml) and stored in an incubator at 25 □ for a certain period. After centrifugation at 10,000 rpm for 10 min, the drug content in the supernatant was measured by HPLC.

Figure 13:
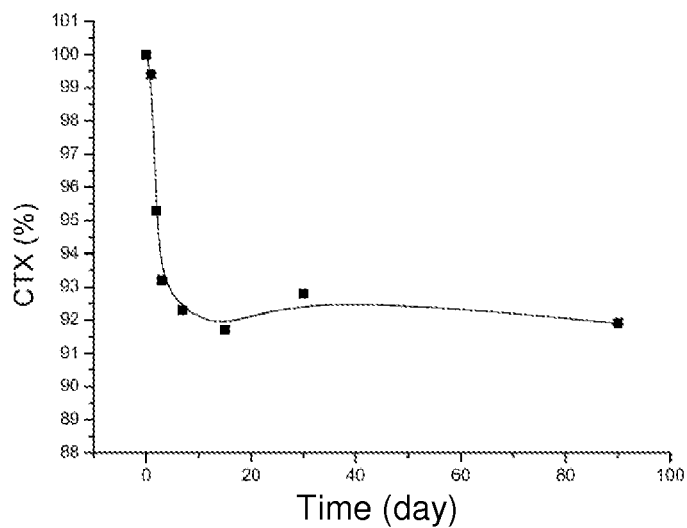
FIG. 13 shows results of the stability test of mPEG$_{2000}$-PLGA$_{2000}$-TB/cabazitaxel micellar solution.

The content variation with time of the drug in a dissolved state was shown in FIG. 13. The content of the dissolved drug in the solution of $mPEG_{2000}$-$PLGA_{2000}$-TB/cabazitaxel micelle was decreased to some extent within the initial 3 days. Later, the release of the drug was much slower. The content of the drug in a dissolved state remained above 90% even over 90 days.

Example 4

Pharmacodynamic Test (1) Inhibition of the docetaxel injection and the lyophilized powder of docetaxel micelle on human lung cancer H460 tumor in nude mouse A. Drugs and Reagents:

The lyophilized powder of docetaxel micelle as prepared in Example 2, provided by Shandong Target Drug Research Co., Ltd., dissolved in 0.9% saline;

Docetaxel Injection, 0.5 ml per tube: 20 mg, produced by Qilu Pharmaceutical Co., Ltd.;

Solvent control (blank micelle, 10 mg/kg), provided by Shandong Target Drug Research Co., Ltd., dissolved in 0.9% saline.

B. Experimental Animals:

BALB/c nu mice, 4-6 weeks old, either sex (depended on the tumors, each test used the same sex), were provided by Beijing HFK Bioscience Co., Ltd., Certificate No.: SCXK (Beijing) 2009-0004.

C. Rearing Facilities:

Barrier housing facilities of Laboratory Animal Center, Institute of Materia Medica, Chinese Academy of Medical Sciences. License number: SYXK (Beijing) 2009-0004; Duration: Feb. 25, 2009-Feb. 25, 2014.

D. Tumor Cell Strains:

Human lung cancer H460 cell from ATCC was cultured in vitro in our laboratory, inoculated in nude mice to form the tumor, and subcultured and preserved.

E. Test Methods

Tumor-bearing animals in good condition and with well-grown H460 tumor were selected and killed by cervical dislocation. The tumor was removed under a sterile condition, cut with a scalpel into pieces of 2-3 mm in diameter, and subcutaneously inoculated with a trocar on nude mice's axilla. 7 to 8 days after the inoculation, the average volume of tumor in the tumor-bearing mice was about 110-120 mm$^3$. The animals were grouped based on the tumor size, with 8 mice in each group.

A negative control group, a solvent control group, a docetaxel injection group (10 mg/kg/time) and a group for the lyophilized powder of docetaxel micelle (10 mg/kg/time base on docetaxel) were set up; wherein the tumor in the animals of the negative control group grew naturally; the solvent used in the solvent control group had the same volume as the group for the lyophilized powder of docetaxel micelle; the docetaxel injection was diluted into the same volume as that of the group for the lyophilized powder of docetaxel micelle; animals in each group were intravenously injected simultaneously.

Starting from the day of grouping, animals in each group were intravenously administered once every other three days as scheduled, for three doses in total. The observation was terminated when the average tumor volume of the negative control group reached about 2,000 mm$^3$.

Experimental Statistics and Evaluation Methods:

(A) Formula for calculating Tumor volume: $V = a \times b^2/2$ (wherein a and b represented length and width, respectively)

(B) The relative tumor volume (RTV) was calculated by the formula: Vt/Vo (wherein Vo was the TV measured on the day of grouping; Vt was the TV measured subsequently)

TV represented tumor volume.

(C) The relative tumor proliferation rate (T/C (%)) was used as the criteria for evaluating the anti-tumor activity, and was calculated by the formula below:

T/C (%)=RTV of the treatment group (T)/RTV of the negative control group (C)×100

(D) The inhibition rate of drugs against tumor growth is calculated by the formula below:

Tumor inhibition rate (%)=(the average tumor weight of the control group−the average tumor weight of the treatment group)/the average tumor weight of the control group×100

(E) Statistical significance of differences of tumor weight, tumor volume, RTV and other criteria among groups was calculated by t-test.

(F) Evaluation Criteria: T/C (%)>40 was determined as inefficacious; T/C (%)≤40 and P<0.05 was determined as efficacious.

F. Results and Conclusions:

Both docetaxel injection group (10 mg/kg/time) and the group for the lyophilized powder of docetaxel micelle (10 mg/kg/time) showed significant inhibition effect against H460 tumor growth in nude mice, and the tumor volumes were significantly decreased. In the group for the lyophilized powder of docetaxel micelle (10 mg/kg/time), the tumor volume was gradually reduced during the administration period; and the tumor volume was maintained lower than the average volume prior to the administration for nearly 10 days. As compared with the docetaxel injection group (10 mg/kg/time), the inhibitory effect on tumor of the docetaxel micelle intravenously injected at the same dosage was significantly improved, wherein the inhibition rate on tumor weight was 68.35% for the former group, and 97.5% for the latter group, the relative tumor proliferation rate was 25.25% for the former group, and 3.78% for the latter group, suggesting that the efficacy was enhanced.

Figure 14:
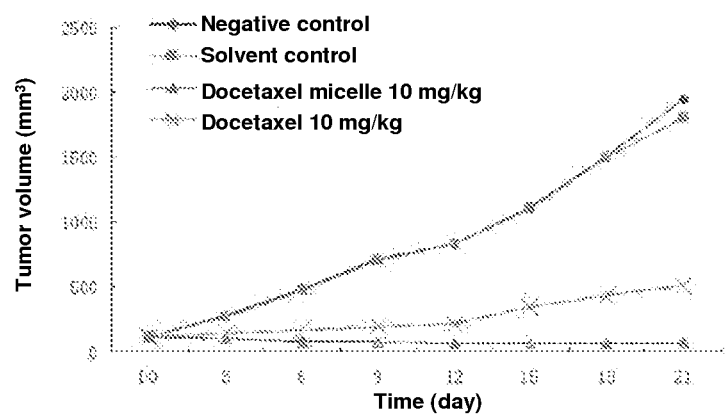
FIG. 14 shows the inhibition of docetaxel injection and docetaxel micellar injection against H460 tumor.
Figure 15:
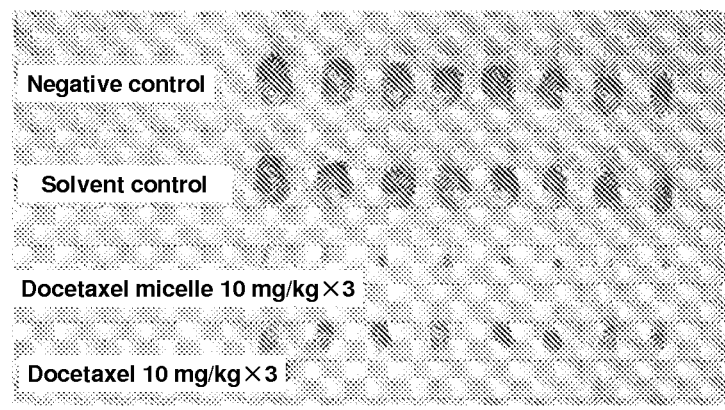
FIG. 15 shows the inhibition of docetaxel injection and docetaxel micellar injection against H460 tumor.

The inhibition effects of docetaxel injection and the lyophilized powder of docetaxel micelle on H460 tumor were shown in FIG. 14 and FIG. 15.

The inhibition rate on H460 tumor of docetaxel injection and the lyophilized powder of docetaxel micelle and the relative tumor proliferation rate were shown in Table 1 and Table 2.

TABLE 1

Inhibition effect of docetaxel injection and the lyophilized powder of docetaxel micelle on H460 tumor

| Group | Number of animals | | Body weight (g) | | Tumor weight | Tumor inhibition |
| --- | --- | --- | --- | --- | --- | --- |
| | Begin | End | Begin | End | (g) | rate (%) |
| negative control group | 8 | 8 | 21.0 ± 1.00 | 24.0 ± 1.41 | 1.72 ± 0.517 | |
| solvent control group | 8 | 8 | 20.9 ± 1.39 | 24.1 ± 1.76 | 1.62 ± 0.510 | 5.81 |
| docetaxel injection group (10 mg/kg) | 8 | 8 | 21.3 ± 0.97 | 23.1 ± 2.20 | 0.545 ± 0.166* | 68.35 |
| docetaxel micelle group (10 mg/kg) | 8 | 8 | 21.6 ± 1.11 | 21.6 ± 2.34 | 0.04 ± 0.018* | 97.5 |

*P < 0.001, compared with the negative control

TABLE 2

Inhibition effect of docetaxel injection and the lyophilized powder of docetaxel micelle on H460 tumor

| Group | Tumor Volume (mm³) Begin | End | RTV | T/C (%) |
|---|---|---|---|---|
| negative control group | 119 ± 25.5 | 1947 ± 748.7 | 16.87 ± 6.684 | |
| solvent control group | 109 ± 20.8 | 1810 ± 481.9 | 16.63 ± 3.179 | 94.02 |
| docetaxel injection group (10 mg/kg) | 121 ± 25.3 | 509 ± 165.4 | 3.93 ± 2.838** | 25.25 |
| docetaxel micelle group (10 mg/kg) | 112 ± 29.0 | 69.3 ± 27.2 | 0.64 ± 0.243** | 3.78 |

*P < 0.01, compared with the negative control;
**P < 0.001, compared with the negative control (2) Inhibition of the docetaxel injection and the lyophilized powder of docetaxel micelle on human breast cancer MDA-MB-231 tumor in nude mice
A. Drugs and Reagents: The Same as in Example 4 (1).
B. Experimental Animals: The Same as in Example 4 (1).
C. Rearing Facilities: The Same as in Example 4 (1).
D. Tumor Cell Strains:
Human breast cancer MAD-MB-231 cell obtained from ATCC was cultured in vitro in our laboratory, inoculated in nude mice to form the tumor, and subcultured and preserved.
E. Test Methods
Tumor-bearing animals in good condition and with well-grown MDA-MB-231 tumor were selected and killed by cervical dislocation. The tumor was removed under a sterile condition, cut with a scalpel into pieces of 2-3 mm in diameter, and subcutaneously inoculated with a trocar on nude mice's axilla. 11 days after inoculation, the average volume of tumor in the tumor-bearing mice was about 110-120 mm³. The animals were grouped based on the tumor size, with 8-9 mice in each group.

A negative control group, a solvent control group, a docetaxel injection group (10 mg/kg/time) and a group for the lyophilized powder of docetaxel micelle (10 mg/kg/time base on docetaxel) were set up; wherein the tumor in the animals of the negative control group grew naturally; the solvent used in the solvent control group had the same volume as the docetaxel micelle group (10 mg/kg dose); the docetaxel injection was diluted into the same volume as that of the group for the lyophilized powder of docetaxel micelle; animals in each group were intravenously injected simultaneously.

Starting from the day of grouping, animals in each group were intravenously administered once every other three days as scheduled, for three doses in total. The observation was terminated when the average tumor volume of the negative control group reached about 2,000 mm³.

Experimental Statistics and Evaluation Methods:
(A) Formula for calculating Tumor volume: $V = a \times b^2/2$ (wherein a and b represented length and width, respectively)
(B) The relative tumor volume (RTV) was calculated by the formula: Vt/Vo
(wherein Vo was the TV measured on the day of grouping; Vt was the TV measured subsequently)
(C) The relative tumor proliferation rate (T/C (%)) was used as the criteria for evaluating the anti-tumor activity, and was calculated by the formula below:

$$T/C\ (\%) = \text{RTV of the treatment group } (T)/\text{RTV of the negative control group } (C) \times 100$$

(D) The inhibition rate of drugs against tumor growth is calculated by the formula below:

Tumor inhibition rate (%) = (the average tumor weight of the control group − the average tumor weight of the treatment group)/the average tumor weight of the control group × 100

(E) Statistical significance of differences of tumor weight, tumor volume, RTV and other criteria among groups was calculated by t-test.
(F) Evaluation Criteria: T/C (%)>40 was determined as inefficacious; T/C (%)≤40 and P<0.05 was determined as efficacious.

F. Results and Conclusions:
Mice bearing the breast cancer MDA-MB-231 tumor in docetaxel injection group (10 mg/kg/time) and the group for the lyophilized powder of docetaxel micelle (10 mg/kg/time) were intravenously injected intermittently for three times. The tumor growth in nude mice was significantly inhibited by the drugs. After administration for three times, the tumor volume was progressively decreased as compared with the volume prior to the administration. The tumor growth was almost stopped in the group for the lyophilized powder of docetaxel micelle (10 mg/kg/time). The inhibition effect on MDA-MB-231 tumor of the group for the lyophilized powder of docetaxel micelle was better as compared with the docetaxel injection group at the same dose.

Figure 16:
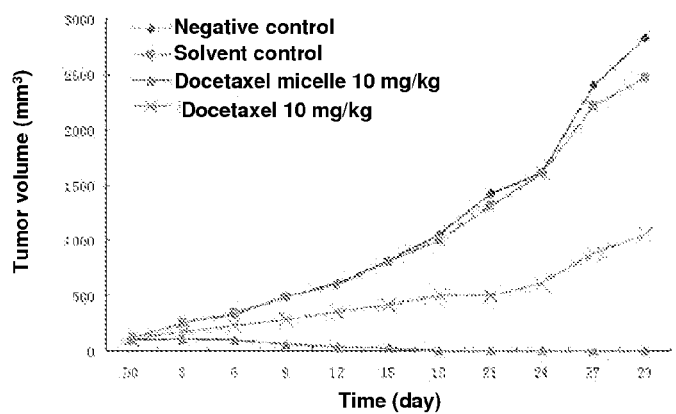
FIG. 16 shows the inhibition of docetaxel injection and docetaxel micellar injection against MDA-MB-231 tumor.
Figure 17:
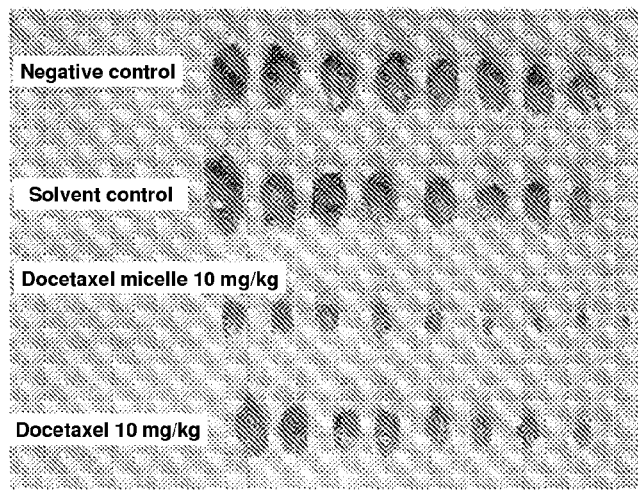
FIG. 17 shows the inhibition of docetaxel injection and docetaxel micellar injection against MDA-MB-231 tumor.

The inhibition effects of docetaxel injection and the lyophilized powder of docetaxel micelle on MDA-MB-231 tumor were shown in FIG. 16 and FIG. 17;

The inhibition rate on MDA-MB-231 tumor of docetaxel injection and the lyophilized powder of docetaxel micelle and the relative tumor proliferation rate were shown in Table 3 and Table 4.

TABLE 3

Inhibition effect of docetaxel injection and the lyophilized powder of docetaxel micelle on MDA-MB-231 tumor

| Group | Number of animals Begin | End | Body weight (g) Begin | End | Tumor weight (g) | Tumor inhibition rate (%) |
|---|---|---|---|---|---|---|
| negative control group | 8 | 8 | 17.1 ± 1.12 | 21.3 ± 0.51 | 2.83 ± 0.735 | |
| solvent control group | 8 | 8 | 17.3 ± 0.99 | 20.8 ± 1.92 | 2.48 ± 0.886 | 12.3 |
| docetaxel injection group (10 mg/kg) | 8 | 8 | 15.8 ± 1.16 | 21.0 ± 1.63 | 1.08 ± 0.646* | 61.8 |
| docetaxel micelle group (10 mg/kg) | 9 | 9 | 17.0 ± 0.71 | 20.1 ± 1.05 | 0.26 ± 0.191* | 90.8 |

*P < 0.01, compared with the negative control

TABLE 4

Inhibition effect of docetaxel injection and the lyophilized powder of docetaxel micelle on MDA-MB-231 tumor

| Group | Tumor Volume (mm³) | | RTV | T/C (%) |
|---|---|---|---|---|
| | Begin | End | | |
| negative control group | 107 ± 22.0 | 2833 ± 782.3 | 28.89 ± 11.371 | |
| solvent control group | 107 ± 27.9 | 1472 ± 904.9 | 27.26 ± 11.779 | 94.41 |
| docetaxel injection group (10 mg/kg) | 107 ± 30.7 | 1054 ± 620.5 | 10.62 ± 5.295* | 36.78 |
| docetaxel micelle group (10 mg/kg) | 101 ± 42.4 | 0 | 1.96 ± 1.448** | 6.79 |

*P < 0.01, compared with the negative control;
**P < 0.001, compared with the negative control Example 5

Figure 18:
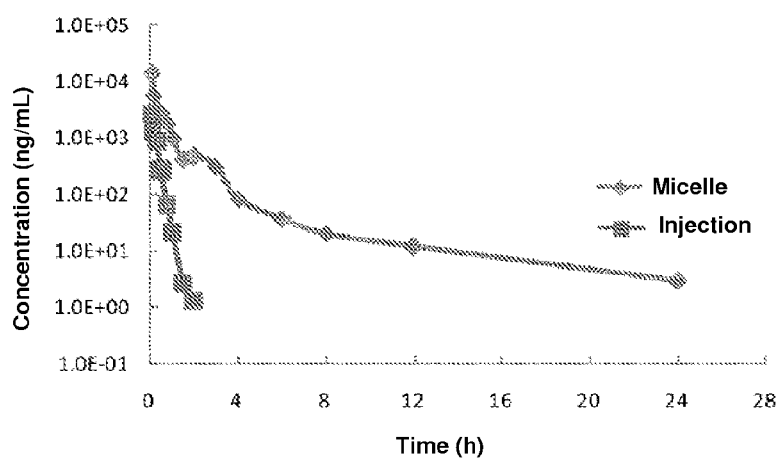
FIG. 18 shows the drug concentration-time curve of docetaxel in plasma from rats iv-administered with docetaxel micelles (5 mg/kg)
Figure 19:
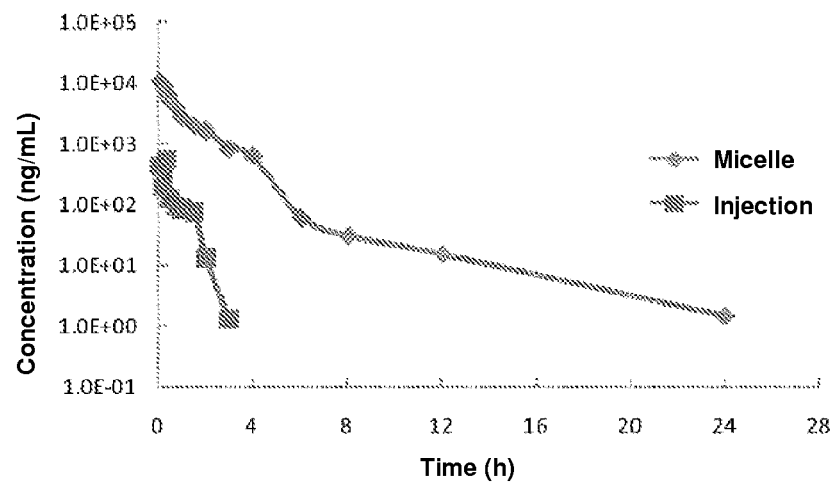
FIG. 19 shows the drug concentration-time curve of cabazitaxel in plasma from rats iv-administered with cabazitaxel micelles (5 mg/kg)

Pharmacokinetics Study (1) Comparative Plasma Pharmacokinetics Study in Rats
A. Experimental Animals:
Male SD rats, with weight of 240±20 g, were randomly divided into four groups (I, II, III, and IV), with 6 rats in each group.
B. Experimental Preparations:
Lyophilized powder of docetaxel micelle (a) was prepared by the procedure of Example 2 (2); batch number: 20120907; specification: 20 mg docetaxel/bottle;
Lyophilized powder of cabazitaxel micelle (b) was prepared by the procedure of Example 2 (3); batch number: 20120830; specification: 20 mg cabazitaxel/bottle;
Dopafei (docetaxel injection, c) was a product from Qilu Pharmaceutical Co., Ltd.; batch number: 1120312TA: specification: 0.5 ml, 20 mg;
Lyophilized powder of cabazitaxel (d), prepared with Tween-80 as a solubilizer.
C. Administration and Sample Collection:
The experimental preparations were dissolved or diluted to a suitable concentration immediately prior to use. 5 mg/kg of docetaxel micelle (a) and cabazitaxel micelle (b) (based on the content of docetaxel and cabazitaxel, respectively) were injected via tail veins to the rats of groups I and II, respectively; 5 mg/kg of docetaxel injection (c) and the lyophilized powder of cabazitaxel (d) were injected via tail veins to the rats of groups III and IV, respectively. Blood samples were taken from the periorbital venous plexus of rats at different time point after the administration, and collected into anticoagulation centrifuge tubes containing heparin, and centrifuged to obtain the plasma. The plasma samples were stored at −80 □ in an untra-low temperature freezer for further use.
D. Plasma Concentration-Time Curves and Pharmacokinetic Parameters:
After precipitated with methanol to remove the protein, the plasma samples were analyzed by LC-MS/MS to determine the total drug concentration of docetaxel or cabazitaxe. The drug concentration in plasma versus time curves of each treatment group were shown in FIG. 18 (the plasma concentration versus time curves of the lyophilized powder of docetaxel micelle (a) and docetaxel injection (c) intravenously administrated to rats) and FIG. 19 (the plasma concentration-time curves of the lyophilized powder of cabazitaxel micelle (b) and the lyophilized powder of cabazitaxel (d) intravenously administrated to rats).

Figure 20:
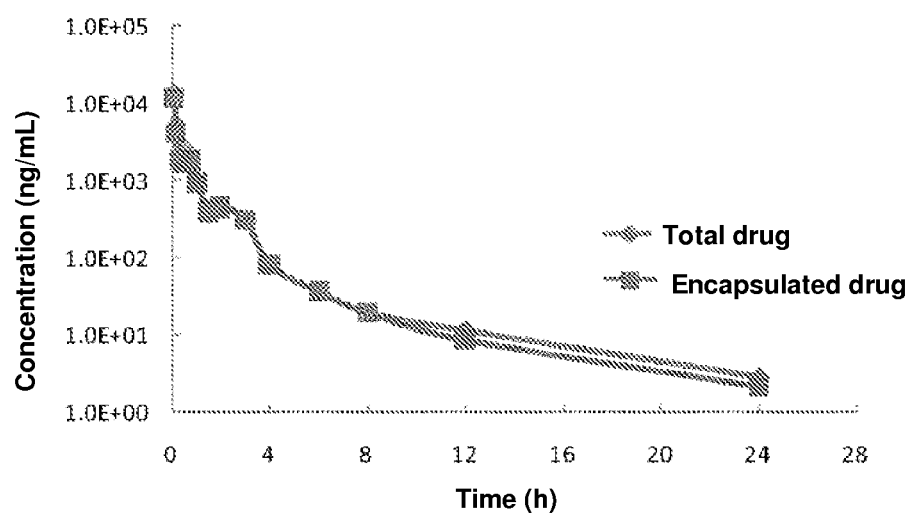
FIG. 20 shows the concentration-time curves of the total amount of the drug and the encapsulated drug of docetaxel in plasma from rats iv-administered with docetaxel micelles (5 mg/kg)
Figure 21:
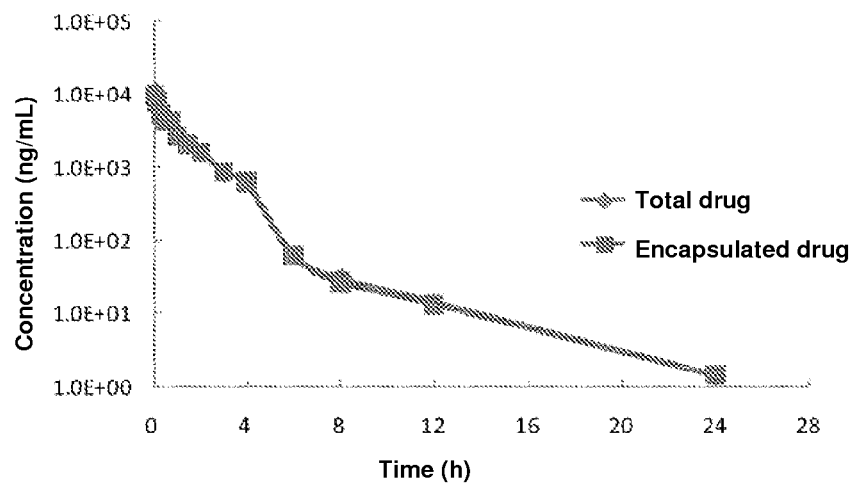
FIG. 21 shows the concentration-time curves of the total amount of the drug and the encapsulated drug of cabazitaxel in plasma from rats iv-administered with cabazitaxel micelles (5 mg/kg)

Meanwhile, after the free drugs were removed by ultrafiltration, the plasma samples were analyzed by LC-MS/MS to determine the concentration of encapsulated docetaxel or cabazitaxel. The concentration-time curves of total drugs and encapsulated drugs in plasma of rats which were iv administered with docetaxel micelle and cabazitaxel micelle were drawn and shown in FIG. 20 (docetaxel micelle, iv 5 mg/kg), and FIG. 21 (cabazitaxel micelle, iv 5 mg/kg).
E. Results:
The results indicated that both of docetaxel micelle group and cabazitaxel micelle group had significantly higher plasma concentration of drug and longer half-life for elimination, as compared with the corresponding injection group. Particularly, the plasma AUC of docetaxel micelle and docetaxel injection (iv, 5 mg/kg, based on docetaxel) were 3,732 ng/mL h and 436 ng/mL h, respectively, and the $t_{1/2}$ were 1.9 h and 0.1 h, respectively. The plasma AUC of cabazitaxel micelle and cabazitaxel injection (iv, 5 mg/kg, based on cabazitaxel) were 4,295 ng/mL h and 482 ng/mL h, respectively, and the $t_{1/2}$ were 2.7 h and 0.3 h, respectively. The plasma AUC of the docetaxel micelle group and cabazitaxel micelle group were 8.56 times and 8.91 times of their corresponding injection groups, respectively. In addition, as shown in FIG. 20 and FIG. 21, both docetaxel micelle and cabazitaxel micelle in plasma were mainly in the form of encapsulated micelle 24 hours after intravenous administration. The plasma pharmacokinetics characteristics of the micelle administration indicates the excellent stability and unique in vivo release properties of the micelles as prepared by the present invention.

Figure 22:
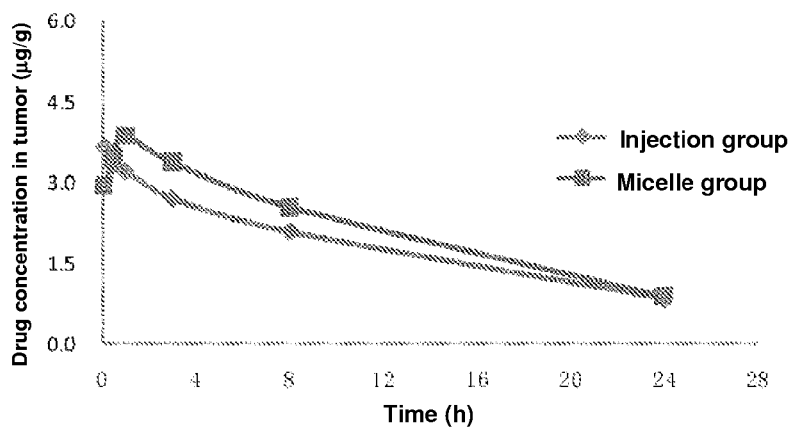
FIG. 22 shows the concentration-time curves of docetaxel (iv 10 mg/kg) in the tumor tissues from tumor-bearing (MX-1) nude mice.

(2) Comparative Study of Drug Distribution in the Tumor Tissues of Tumor-Bearing Mice
A. Experimental Animals:
Female nude mice, which were inoculated with MX-1 human breast cancer cell in the axilla at a density of $5 \times 10^6$, were randomly divided into two groups after the tumors grew to the volume of about 500 mm³ (Group I: group for the lyophilized powder of docetaxel micelle, Group II: group of docetaxel injection). The body weights of mice in the two groups were 24.9±1.2 g and 25.0±1.3 g, respectively, with no significant difference (P>0.05). Each group was then evenly divided into seven sub-groups, and each sub-group had 10 tumor-bearing mice.
B. Experimental Preparations:
Lyophilized powder of docetaxel micelle was prepared by the procedure of Example 2 (2); batch number: 20120907; specification: 20 mg/bottle;
Dopafei (docetaxel injection) was a product from Qilu Pharmaceutical Co., Ltd.; batch number: 1120312TA: specification: 0.5 ml, 20 mg.
C. Administration and Sample Collection:
Docetaxel injection and the lyophilized powder of docetaxel micelle were dissolved or diluted to a suitable concentration immediately prior to use, and were injected via tail veins to the animals in groups I and II at a dosage of 10 mg/kg (based on docetaxel), respectively. Mice in each group were sacrificed 5 min, 15 min, 30 min, 1 h, 3 h, 8 h and 24 h after the administration, and the tumor tissues were scrapped, weighed, and stored at −80 □ in an ultra low temperature freezer for further use.
D. Drug Distribution in Tumor Tissues:
After homogenation, the tumor tissues were analyzed by LC-MS/MS to determine the concentration of docetaxel. The concentration-time curves of drugs in tumor tissues from each treatment group were shown in FIG. 22. With the same dose (10 mg/kg), the AUC of docetaxel in the tumor tissues of nude mice within 24 h after administration were 45.528 mg/L h for the injection group (Group I) and 57.089 mg/L h for the micelle group (Group II). These results showed that the drug distribution in tumor tissue for the docetaxel micelle group was significantly higher than that of the docetaxel injection group (P<0.01), and the difference was 25.4%.

The examples as described above are preferred embodiments of the present invention. However, the embodiments of the present invention are not limited by the above examples. Any variations, modifications, replacements, combinations and simplifications to the invention without departing from the spirit or principle of the present invention are equivalents of the present invention, and included within the scope of the present invention.

Example 6

Comparative Study on In Vivo and In Vitro Stability of Boc-Phenylalanine-Endcapped mPEG$_{2000}$-PLA$_{1800}$ Copolymer/Paclitaxel Micelle and Benzoyl-Endcapped mPEG$_{2000}$-PLA$_{1800}$ Copolymer/Paclitaxel Micelle (1) Preparation of copolymers: Benzoyl-endcapped mPEG$_{2000}$-PLA$_{1800}$ copolymer was synthesized by the method as described in CN01809632.8. mPEG$_{2000}$-PLA$_{1800}$-BP was synthesized by the method as described in Example 1 (2) of the present application. Paclitaxel micelles were prepared with either of the two copolymers as an excipient and with paclitaxel as a drug.

(2) Preparation of micelles: 150 mg of copolymer and 30 mg of paclitaxel were dissolved in 5 ml of ethanol. The solvent was removed by rotary evaporation at 45° C. Then, 5 ml of saline was added to dissolve the drug. The obtained solution was filtered through a 0.22 μm membrane and stored at 37° C., and the stability was observed.

(3) Method for testing stability: The micellar solution was injected into the blood of rats via tail vein; the blood samples were taken at different time point, and were subjected to high performance liquid chromatography to determine the paclitaxel content in the blood.

Figure 23:
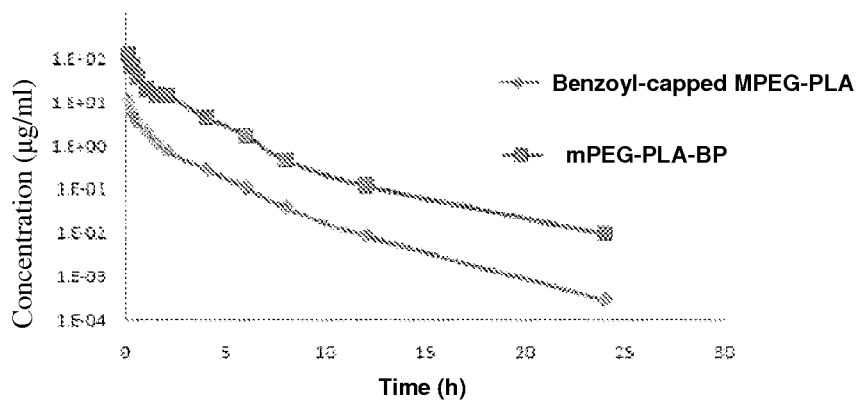
FIG. 23 shows the drug concentration-time curves of paclitaxel in plasma from rats iv-administered with mPEG$_{2000}$-PLA$_{1800}$-BP/paclitaxel micelles and benzoyl-capped mPEG$_{2000}$-PLA$_{1800}$/paclitaxel micelles.

(4) Results and conclusions: The drug concentration in plasma-time curves of the two micelles was shown in FIG. 23, wherein the plasma concentration of mPEG$_{2000}$-PLA$_{1800}$-BP/paclitaxel micelle group was significantly higher than that of benzoyl-capped mPEG$_{2000}$-PLA$_{1800}$ copolymer/paclitaxel micelle group, and more than 80% of the drug was encapsulated in the micelles, indicating the excellent in vivo stability. No drug precipitation was observed for mPEG$_{2000}$-PLA$_{1800}$-BP/paclitaxel micelle over a period of at least 48 h, while for benzoyl-capped mPEG$_{2000}$-PLA$_{1800}$ copolymer/paclitaxel micelle, significant drug precipitation occurred after 17 h, indicating that the stability of mPEG$_{2000}$-PLA$_{1800}$-BP/paclitaxel micelle was significantly higher than that of benzoyl-capped mPEG$_{2000}$-PLA$_{1800}$/paclitaxel micelle.

The invention claimed is:

1. A micellar drug-loaded system, comprising at least one amphiphilic block copolymer, at least one anti-tumor drug with a therapeutically effective amount, and a pharmaceutically acceptable pharmaceutical auxiliary agent; wherein said amphiphilic block copolymer comprises a hydrophilic segment and a hydrophobic segment wherein said hydrophilic segment is polyethylene glycol or methoxypolyethylene glycol with the number-average molecular weight in the range of 750 to 5000; said hydrophobic segment is selected from the group consisting of polylactide, polyglycolide, poly(lactic-co-glycolic acid), polycaprolactone, polycarbonate and polydioxanone, each has a number-average molecular weight in the range of 1000 to 50000 and is end-capped with a hydrophobic group, wherein said hydrophobic group is t-butoxycarbonyl phenylalanine.

2. The micellar drug-loaded system of claim 1 wherein said amphiphilic block copolymer is prepared by a method comprising the steps of:
adding a hydrophilic segment with a number-average molecular weight in the range of 400 to 20000 to a flask for polymerization; heating to 100° C.-130° C. and dehydrating under vacuum for 2 h-4 h; then adding the monomer of the hydrophobic segment and stannous octoate as the catalyst, wherein the weight of stannous octoate is 0.3%-1% of said monomer; sealing the flask under vacuum, carrying out reaction with the above reactants at 100° C.-150° C. for 12 h-24 h; then dissolving with dichloromethane; adding diethyl ether to thoroughly precipitate a polymer, then filtrating and drying under vacuum to obtain the block copolymer composed of the hydrophilic segment and the hydrophobic segment, wherein said hydrophilic segment is polyethylene glycol or methoxypolyethylene glycol;
dissolving the block copolymer composed of the hydrophilic segment and the hydrophobic segment in ethyl acetate, tetrahydrofuran, dichloromethane, ethyl acetate or double distilled water; then adding t-butoxycarbonyl phenylalanine to carry out the reaction for converting the terminal hydroxyl group into a hydrophobic group; filtrating to remove insoluble substance, adding sufficient amount of diethyl ether to precipitate a polymer; filtrating and drying under vacuum to obtain the copolymer.

3. The micellar drug-loaded system of claim 1, wherein the weight ratio of the amphiphilic block copolymer to the drug is in the range of 99.5:0.5 to 50:50.

4. The micellar drug-loaded system of claim 3, wherein the weight ratio of the amphiphilic block copolymer to the drug is in the range of 99:1 to 75:25.

5. The micellar drug-loaded system of claim 1, wherein said pharmaceutical auxiliary agent is an excipient for lyophilization.

6. The micellar drug-loaded system of claim 5, wherein said excipient for lyophilization is at least one of lactose, mannitol, sucrose, trehalose, fructose, glucose, sodium alginate and gelatin.

7. The micellar drug-loaded system of claim 5, wherein said excipient for lyophilization accounts for 0 to 99.9% of the entire system by weight.

8. The micellar drug-loaded system of claim 7, wherein said excipient for lyophilization accounts for 10.0% to 80.0% of the entire system by weight.

9. The micellar drug-loaded system of claim 1, wherein said pharmaceutical auxiliary agent further comprises an antioxidant, metal ion complexing agent, pH adjusting agent or isotonicity adjusting agent; said antioxidant is sodium sulfite, sodium bisulfite or sodium metabisulfite; said metal ion complexing agent is edetate disodium, calcium disodium edetate or sodium cyclohexylenediamine tetraacetate; said pH adjusting agent is citric acid, sodium bicarbonate, disodium hydrogen phosphate or sodium dihydrogen phosphate; and said isotonicity adjusting agent is sodium chloride or glucose.

10. The micellar drug-loaded system of claim 1, wherein said anti-tumor drug is at least one of paclitaxel, docetaxel, cabazitaxel, larotaxel, curcumin, doxorubicin and epirubicin.

11. A method for preparing a micellar drug-loaded system according to claim 1, wherein said method is a dialysis method, a direct dissolution method, a film hydration method, a solid dispersion method or a high-energy homo-emulsification method.

12. The method of claim 11, wherein said method is a film hydration method and wherein the steps of said film hydration method includes: dissolving the polymer and the drug in organic solvent; removing the solvent by rotary evaporation; then adding water for injection to dissolve drug film so as to get the solution of the drug-loaded micelle; and obtaining the lyophilized powder of the micelle after sterilization by filtration and lyophilization.

13. The method of claim 11, wherein said method is a solid dispersion method and wherein the steps of said solid dispersion method includes: dissolving the drug in the polymer which is in a molten state upon heating to give a clear mixture; adding water for injection to dissolve and get the solution of the micelle; and obtaining the lyophilized powder of the micelle after sterilization by filtration and lyophilization.

* * * * *